United States Patent
Chien

(10) Patent No.: US 8,978,656 B2
(45) Date of Patent: Mar. 17, 2015

(54) TUBE-POSITIONING DEVICE FOR A BREATHING MASK

(75) Inventor: Chih-Tsan Chien, New Taipei (TW)

(73) Assignee: Apex Medical Corp., New Taipei (TW)

( * ) Notice: Subject to any disclaimer, the term of this patent is extended or adjusted under 35 U.S.C. 154(b) by 714 days.

(21) Appl. No.: 13/338,317

(22) Filed: Dec. 28, 2011

(65) Prior Publication Data

US 2013/0068231 A1 Mar. 21, 2013

(51) Int. Cl.
  *A62B 18/08* (2006.01)
  *A61M 16/00* (2006.01)
  *A61M 16/04* (2006.01)
  *A61M 16/06* (2006.01)

(52) U.S. Cl.
  CPC .......... *A62B 18/08* (2013.01); *A61M 16/0497* (2013.01); *A61M 16/0683* (2013.01); *A62B 18/084* (2013.01); *A61M 16/0666* (2013.01)
  USPC .................. 128/207.11; 128/207.17

(58) Field of Classification Search
  CPC ............. A61M 16/0488; A61M 16/0497; A61M 16/06; A61M 16/0666; A61M 16/0683
  USPC ........... 128/207.18, 207.11, 206.27, 202.27, 128/200.26, 207.13, 912, 204.11, 128/206.21–206.29; 248/75, 81, 82, 83, 84, 248/85, 87, 88, 521, 74.1, 74.2, 65
  See application file for complete search history.

(56) References Cited

U.S. PATENT DOCUMENTS

| 4,009,720 | A | * | 3/1977 | Crandall | 128/207.15 |
| 4,025,015 | A | * | 5/1977 | Kolic | 248/205.3 |
| 5,067,496 | A | * | 11/1991 | Eisele | 128/207.15 |
| 5,390,669 | A | * | 2/1995 | Stuart et al. | 128/207.14 |
| 6,578,576 | B1 | * | 6/2003 | Taormina et al. | 128/207.17 |
| 6,595,214 | B1 | * | 7/2003 | Hecker et al. | 128/207.13 |
| 7,341,061 | B2 | * | 3/2008 | Wood | 128/207.29 |
| 7,931,026 | B2 | * | 4/2011 | Ho et al. | 128/207.11 |
| 2002/0011248 | A1 | * | 1/2002 | Hansen et al. | 128/207.11 |
| 2006/0213521 | A1 | * | 9/2006 | Radney | 128/207.11 |

FOREIGN PATENT DOCUMENTS

EP  356683 A1 * 3/1990 ........... A61M 25/02

* cited by examiner

*Primary Examiner* — Lynne Anderson
*Assistant Examiner* — Bradley Philips
(74) *Attorney, Agent, or Firm* — Ming Chow; Sinorica, LLC

(57) ABSTRACT

A tube-positioning device mounted on a breathing mask and holding a breathing tube has a headgear buckle and a tube retainer. The headgear buckle has a pivot bracket formed thereon and having a pivot hole defined through the pivot bracket and an annular groove defined radially in the pivot bracket. The tube retainer is mounted detachably and rotatably on the headgear buckle and has two resilient arms, a clamping recess, a pivot shaft and two hooking arms. The resilient arms are curved and the clamping recess is formed between the resilient arms. The hooking arms are formed respectively on and protrude down from the resilient arms and detachably engage and hook in the annular groove of the pivot bracket. Pressing the resilient arms toward each other disengages the hooking arms from the annular groove to rapidly detach the tube retainer from the headgear buckle.

10 Claims, 9 Drawing Sheets

TUBE-POSITIONING DEVICE FOR A BREATHING MASK

BACKGROUND OF THE INVENTION

1. Field of the Invention

The present invention relates to a positioning device, and more particularly to a tube-positioning device that is mounted on a breathing mask and positions a breathing tube of the breathing mask. Components of the tube-positioning device are assembled or detached quickly for maintenance purposes.

2. Description of Related Art

Breathing mask form an interface between a patient and apparatus providing a supply of pressurized air. For the consideration of safety and convenience, a tube-positioning device is needed for the breathing mask. The tube-positioning device has a headgear buckle and a tube retainer. The headgear buckle is mounted on a strap of a mask and is placed on the top of a patient's head and has a mounting hole. The tube retainer has a mounting post mounted rotatably and hooking in the mounting hole of the headgear buckle. Therefore, the tube retainer is able to rotate relative to the headgear buckle. The tube retainer may clamp and position a breathing tube.

However, the mounting post of the tube retainer is designed only for easily extending in the mounting hole of the headgear buckle, not built for quickly separating from the headgear buckle. When the tube retainer is too loose to hold the breathing tube due to material fatigue or aging, replacing the tube retainer from the tube-positioning device is inconvenient and laborious.

To overcome the shortcomings, the present invention provides a tube-positioning device for a breathing mask to mitigate or obviate the aforementioned problems.

SUMMARY OF THE INVENTION

The main objective of the invention is to provide a tube-positioning device that is mounted on a breathing mask and positions a breathing tube of the breathing mask. Components of the tube-positioning device are assembled or detached quickly for maintenance purposes. Furthermore, the assembled tube-positioning device is not disassembled when pulled by an inadvertent dragging force.

A tube-positioning device in accordance with the present invention is mounted on a breathing mask, holds a breathing tube and comprises a headgear buckle and a tube retainer. The headgear buckle has a pivot bracket formed thereon and having a pivot hole defined through the pivot bracket and an annular groove defined radially in the pivot bracket. The tube retainer is mounted detachably and rotatably on the headgear buckle and has two resilient arms, a clamping recess, a pivot shaft and two hooking arms. The resilient arms are curved and the clamping recess is formed between the resilient arms. The hooking arms are formed respectively on and protrude down from the resilient arms and detachably engage and hook in the annular groove of the pivot bracket. Pressing the resilient arms toward each other disengages the hooking arms from the annular groove to rapidly detach the tube retainer from the headgear buckle.

Other objectives, advantages and novel features of the invention will become more apparent from the following detailed description when taken in conjunction with the accompanying drawings.

DETAILED DESCRIPTION OF THE PREFERRED EMBODIMENT

Figure 1:
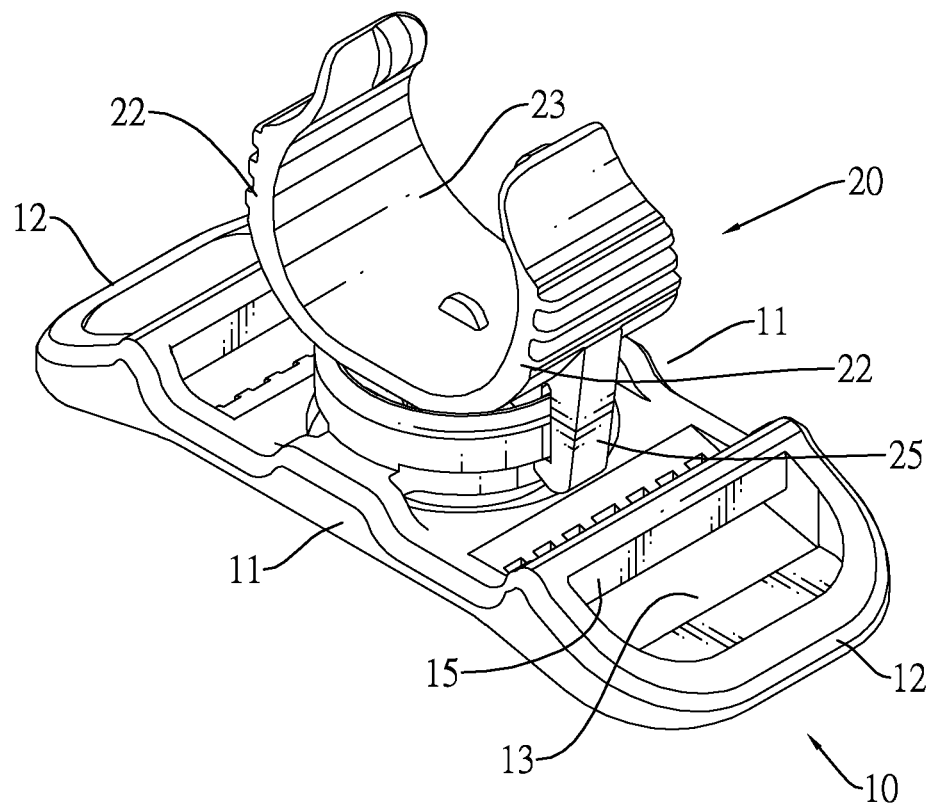
FIG. 1 is a top perspective view of a tube-positioning device for a breathing mask in accordance with the present invention.
Figure 2:
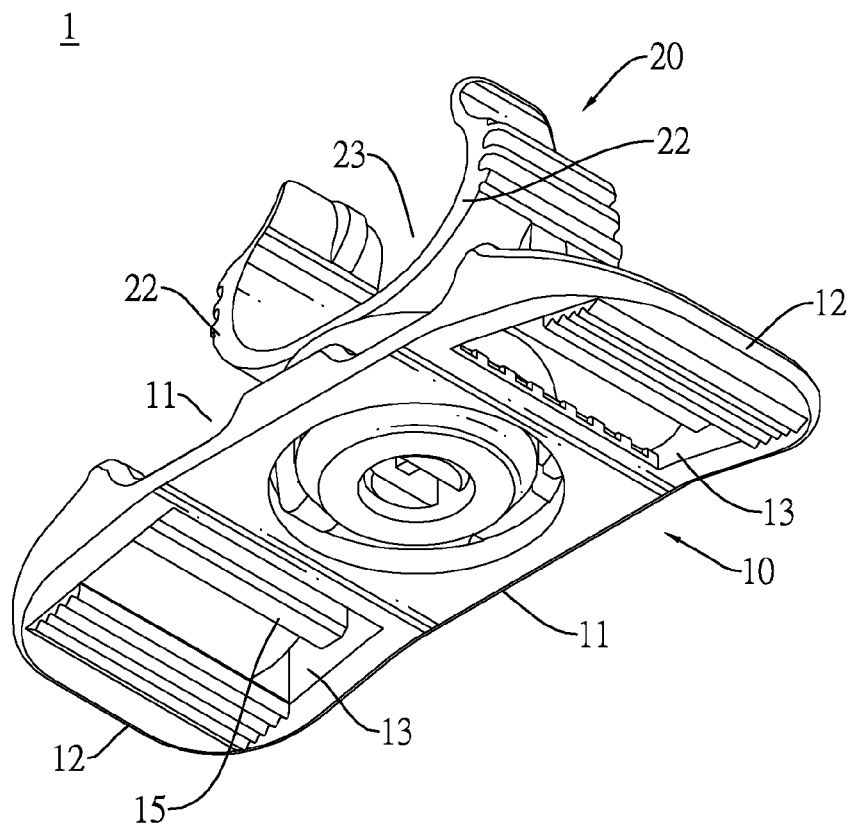
FIG. 2 is a bottom perspective view of the tube-positioning device in FIG. 1.

With reference to FIGS. 1 and 2, a tube-positioning device 1 for a breathing mask in accordance with the present invention comprises a headgear buckle 10 and a tube retainer 20.

Figure 3:
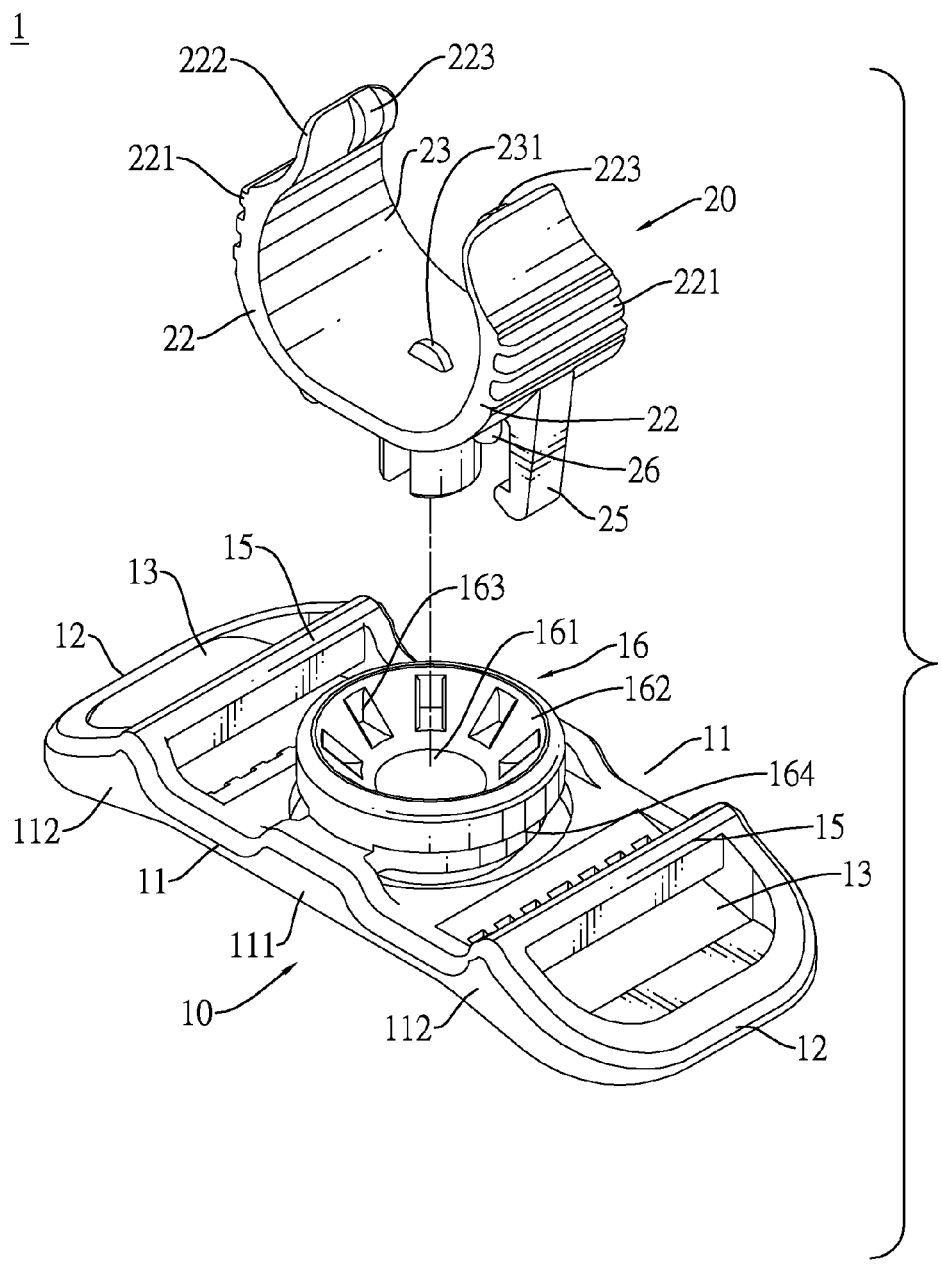
FIG. 3 is an exploded top perspective view of the tube-positioning device in FIG. 1.
Figure 4:
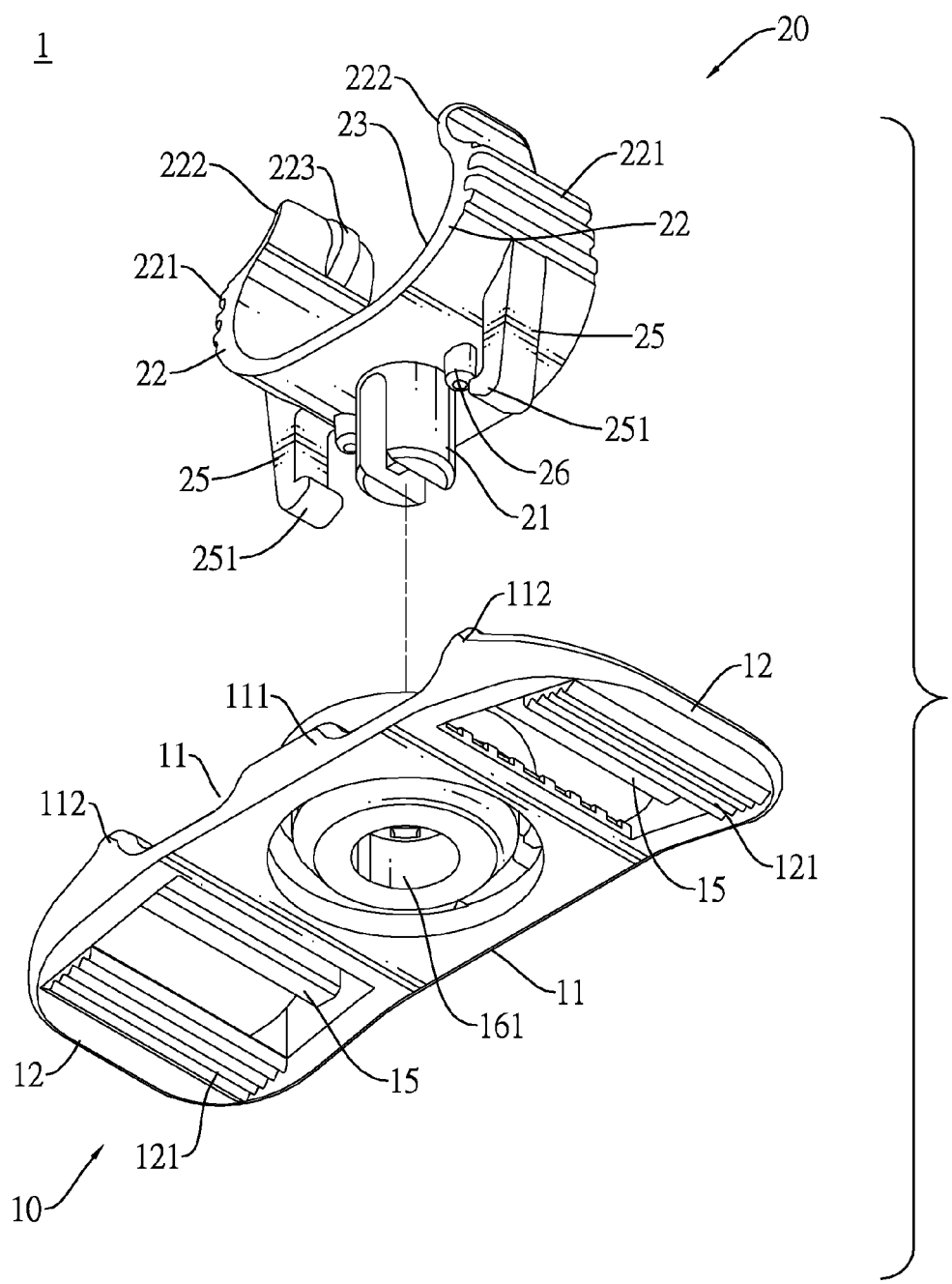
FIG. 4 is an exploded bottom perspective view of the tube-positioning device in FIG. 2.

With further reference to FIGS. 2 to 4, the headgear buckle 10 has two opposite first sides 11, two opposite second sides 12, two assembling holes 13, two crossbeams 15 and a pivot bracket 16.

The second sides 12 are formed between the first sides 11.

The crossbeams 15 are formed between the first sides 11 and are located respectively above the assembling holes 13.

In a preferred embodiment, a thickness of an intervening section between a central section 111 of each first side 11 and a jointing section 112 at which one crossbeam 15 is connected to the first side 11 is smaller than a thickness of the central section 111. Therefore, the thickened intervening section on each first side 11 is somewhat resilient and makes the headgear buckle 10 sufficiently flexible to adapt to a patient's head shape.

Furthermore, each second side 12 may have a bottom surface and a skidproof member 121 formed on the bottom surface. The skidproof member 121 may have multiple ribs to prevent the strap contacting the skidproof member 121 from slipping inadvertently.

The assembling holes 13 are defined through the headgear buckle 10 and are located respectively adjacent to the second sides 12. Each assembling hole 13 allows a strap to extend therethrough so that the strap may be connected to the headgear buckle 10.

The pivot bracket 16 is formed on the headgear buckle 10, is located between the assembling holes 13 and between the crossbeams 15 and has a top, an outer surface, a pivot hole 161, an annular groove 164 and a recess 162. The pivot hole 161 is defined through the pivot bracket 16. The annular groove 164 is defined radially in the outer surface. The recess 162 is funnel-shaped, is defined in the top, communicates with the pivot hole 161 and has an annular inclined surface and multiple positioning slots 163. The positioning slots 163 are defined in the annular inclined surface and are arranged circularly.

Figure 5:
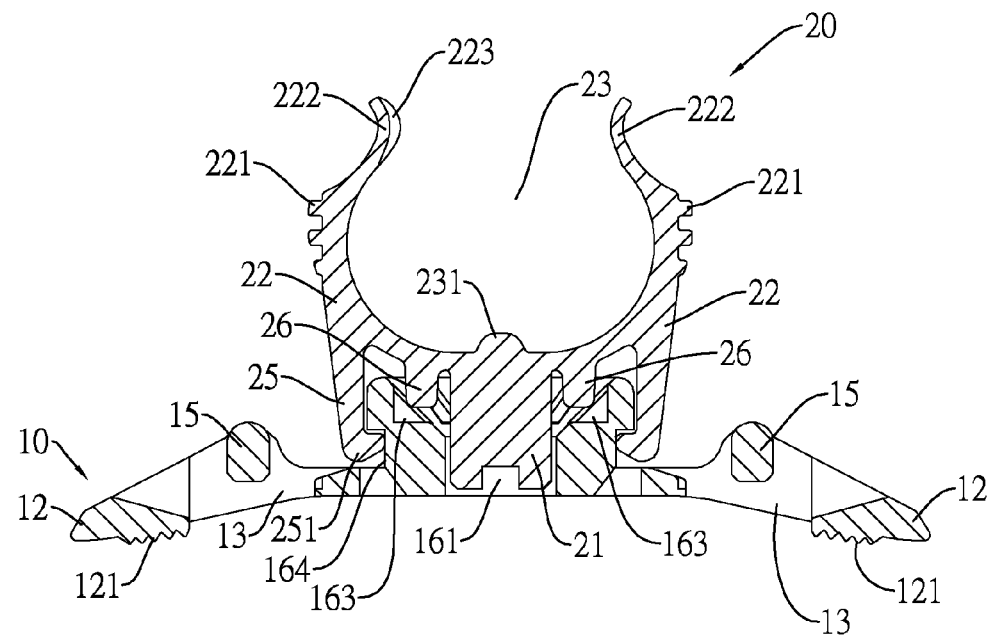
FIG. 5 is a cross sectional front view of the tube-positioning device in FIG. 1.

With further reference to FIG. 5, the tube retainer 20 is mounted rotatably and detachably on the headgear buckle 10 and has two resilient arms 22, a pivot shaft 21, a clamping recess 23, two hooking arms 25, two positioning stubs 26, two resilient tabs 222 and at least one positioning rib 223.

The resilient arms 22 are curved. Each resilient arm 22 has a top end, a bottom edge, an inside concave surface, an outside convex surface and a skidproof section 221. The skidproof section 221 is formed on the outside convex surface and allows a user to hold the resilient arm 22 by fingers without inadvertent slip. The skidproof section 221 has multiple skidproof ribs.

The pivot shaft 21 is formed on and protrudes down from the bottom edges of the resilient arms 22 and is mounted rotatably in the pivot hole 161 of the pivot bracket 16. The resilient arms symmetrically extend outward from a top of the pivot bracket 21.

The clamping recess 23 is formed between the inside concave surfaces of the resilient arms 22 and may have a positioning tab 231 formed in the clamping recess 23.

The hooking arms 25 are formed on and protrude respectively down from the bottom edges of the resilient arms 22 and each hooking arm 25 has a hook 251. The hook 251 is formed on and protrudes from the hooking arms 25 and detachably engages the annular groove 164 of the pivot bracket 16 of the headgear buckle 10. Pressing the resilient arms 22 of the tube retainer 20 toward each other by fingers quickly disengages the hooks of the hooking arms 25 from the annular groove 164 of the pivot bracket 16 and detaches the tube retainer 20 from the headgear buckle 10.

The positioning stubs 26 are formed respectively on and protrude down from the bottom edge of the resilient arms 22 and detachably engage the positioning slots 163 of the headgear buckle 10 respectively.

The resilient tabs 222 are curved and are formed respectively on the top ends of the resilient arm 22. Each resilient tab 222 is thinner than each resilient arm 22 to increase flexibility and facilitate deformation and has an inside convex surface and an outside concave surface. Therefore, a breathing tube may be guided by the inside convex surfaces to move into the clamping recess 23. When the breathing tube is completely inserted in the clamping recess 23, the resilient tabs 222 block and prevent the breathing tube from falling out of the clamping recess 23 inadvertently.

The positioning ribs 223 are formed respectively on the inside convex surfaces of the resilient tabs 222 and are staggered along a front-rear direction to further maintain the breathing tube in the clamping recess 23.

In a preferred embodiment, a height of the annular groove 164 along an axis of the pivot bracket 16 is larger than a height of the hook 251 of each hooking arm 25 so that the hooking arms 25 quickly engage or separate from the annular groove 164.

Figure 6:
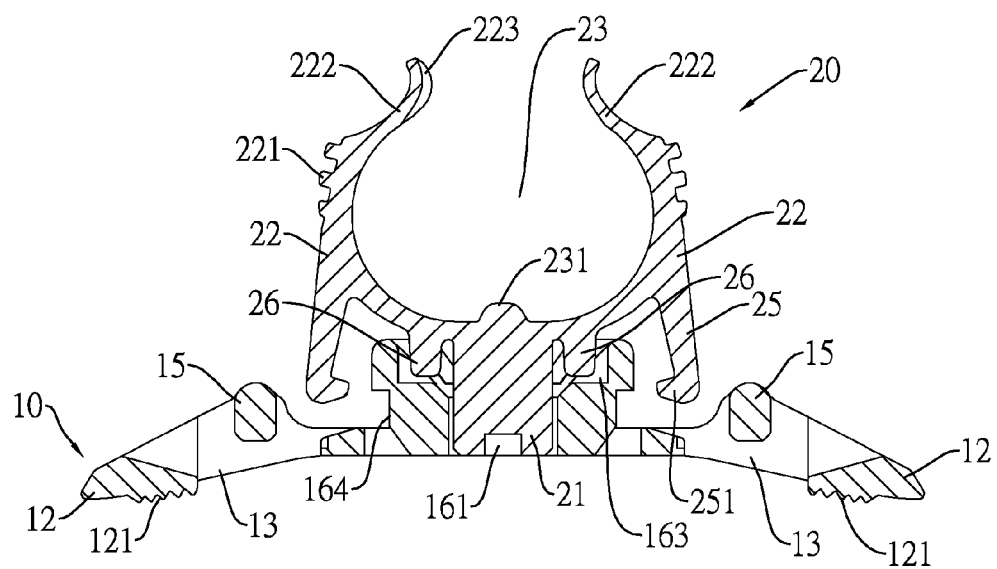
FIG. 6 is an operational cross sectional front view of the tube-positioning device in FIG. 5 showing that the resilient arms of the tube retainer are pressed toward each other and simultaneously the hooking arms move outward away from each other.
Figure 7:
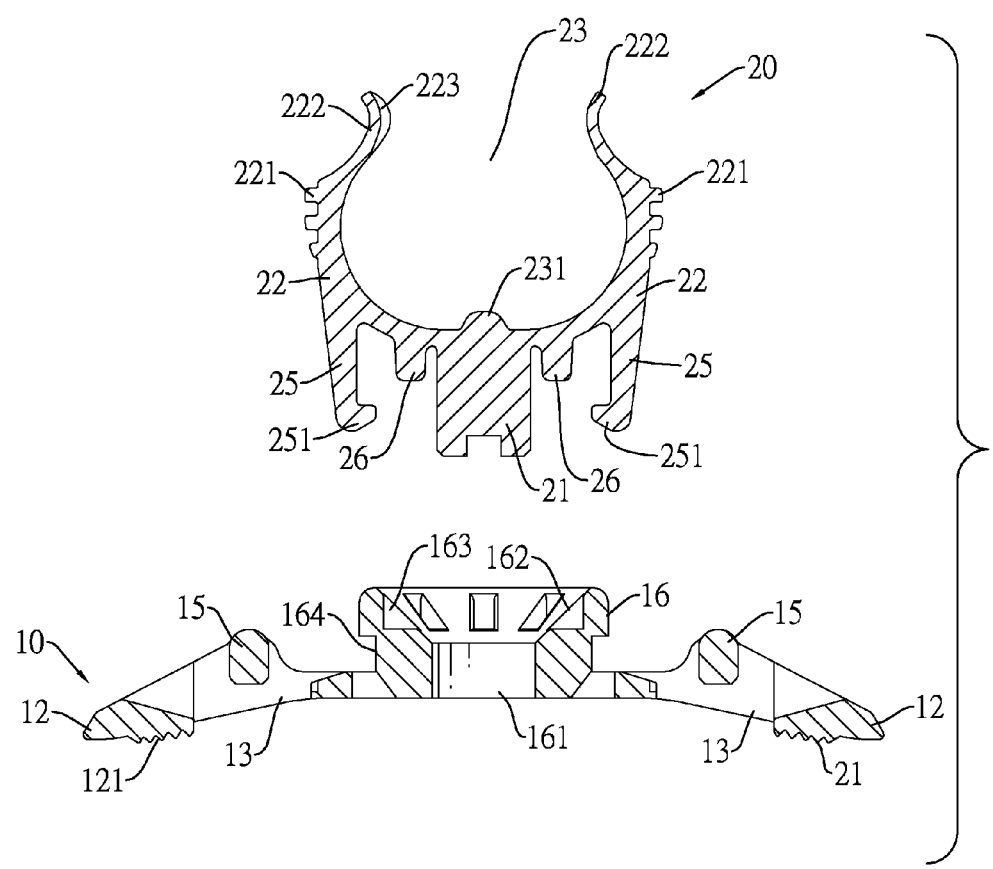
FIG. 7 is an operational cross sectional front view of the tube-positioning device in FIG. 6 showing that the tube retainer is entirely detached from a headgear buckle.
Figure 8:
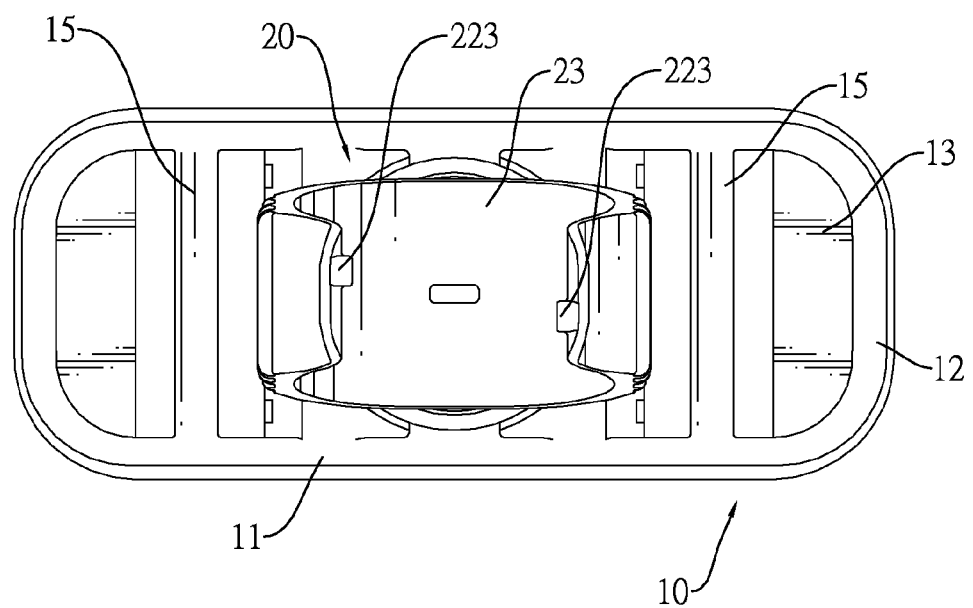
FIG. 8 is a top view of the tube-positioning device in FIG. 1.

With further reference to FIGS. 6 and 7, when detaching the tube retainer 20 from the headgear buckle 10, a user presses the resilient arms 22 toward each other by fingers, which simultaneously makes the hooking arms 25 move outward away from each other. The hooks 251 of the hooking arms 25 are quickly disengaged from the annular groove 164 of the pivot bracket 16. Detaching the tube retainer 20 from the headgear buckle 10 by fingers is quick and convenient without requiring any additional tools.

When the tube retainer 20 engages the headgear buckle 10, the positioning stubs 26 correspond to at least one positioning slot 163 to position the tube retainer 20 at a specific rotational position relative to the headgear buckle 10. Because a position of a breathing device connected to the breathing tube relative to a patient wearing the breathing mask with the tube-positioning device 1 may be changed anytime, timely adjusting the rotational position of the tube retainer 20 relative to the headgear buckle 10 to prevent the breathing tube on the tube-positioning device 1 from curving or twisting is necessary. The tube-positioning device 1 of the present application allows the user to quickly rotate and position the tube retainer 20 on the headgear buckle 10 and therefore facilitates the adjustment of orientation and position of the breathing tube clamped on the tube-positioning device 1. The patient can rest and sleep well without being disturbed by the twisted breathing tube. Furthermore, because the annular groove 164 is formed radially in the outer surface of the pivot bracket 16 to allow the tube retainer 20 to rotate freely, the positioning stub 26 is able to engage different positioning slots 163 of the headgear buckle 10 so that the tube retainer 20 can rotate in multi-stage.

Figure 9:
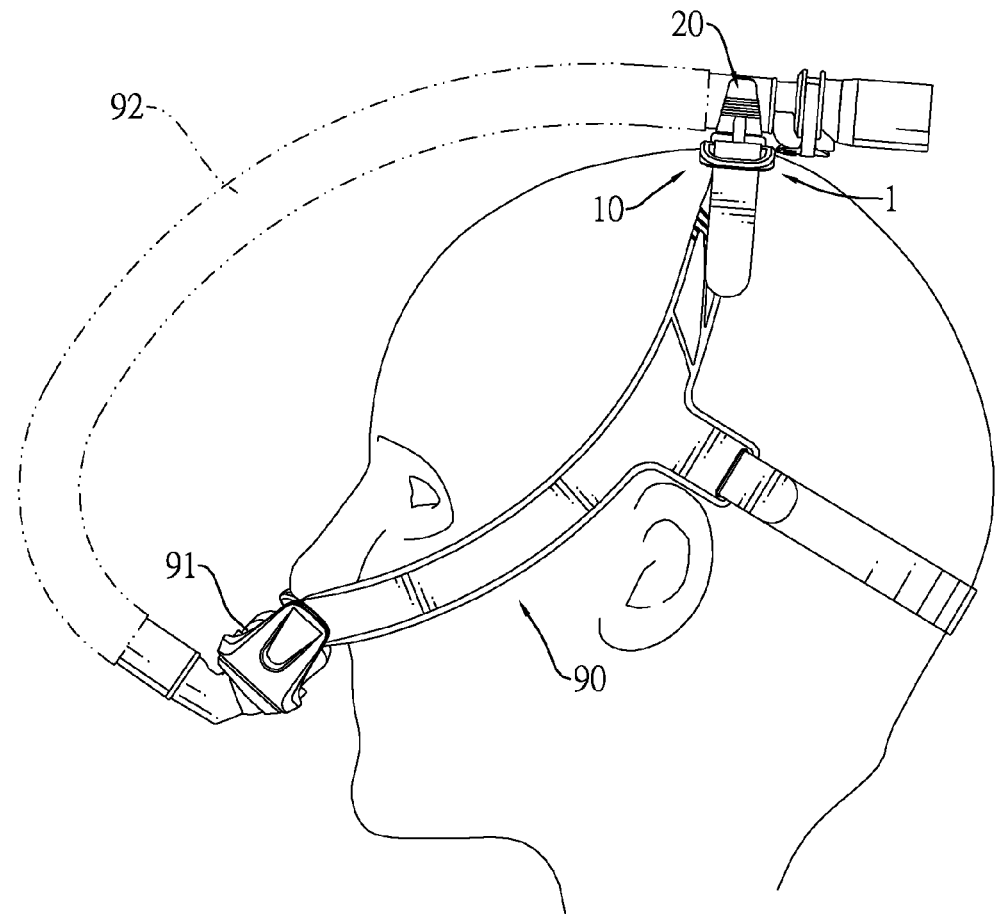
FIG. 9 is a side view of the tube-positioning device mounted on a head strap of a breathing mask worn on a patient's head, wherein a breathing tube of the breathing mask is positioned by the tube retainer.

With further reference to FIG. 9, the tube-positioning device 1 may be mounted on a head strap of a breathing mask 90. The breathing mask 90 includes a mask hub 91 mounted on the head strap. A breathing tube 92 is connected to the mask hub 91 and may be clamped and positioned by the tube retainer 20 to prevent accidental fall or swing.

The present invention has the following advantages:

1. The headgear buckle 10 and tube retainer 20 may be assembled or detached quickly. Pressing the resilient arms 22 of the tube retainer 20 by fingers quickly disengages the hooking arms 25 from the pivot bracket 16 and detaches the tube retainer 20 from the headgear buckle 10.

2. The tube retainer 20 is rotatable relative to the headgear buckle 10. Because a position of a breathing device connected to the breathing tube relative to a patient wearing the breathing mask with the tube-positioning device 1 is changed anytime, timely rotating and positioning the tube retainer 20 relative to the headgear buckle 10 prevent the breathing tube 92 clamped on the tube-positioning device 1 from curving or twisting. Thus, the breathing device connecting to the tube-positioning device 1 is assured to smoothly convey air or oxygen.

3. Because the thickness of the intervening section is smaller than those of the central section 111 on the headgear buckle 10, the headgear buckle 10 has sufficient flexibility to adapt to a patient's head shape.

4. Because the breathing tube 92 has spiral shaped bumps formed on an outer surface thereof, the staggered positioning ribs 223 of the resilient arm 22 and the positioning tab 231 of the clamping recess 23 stably hold and position any section of the breathing tube 92 without inadvertent slip. Pulling the breathing tube 92 relative to the tube-positioning device 1 allows the breathing tube 92 to be positioned at a different section thereof to adapt to a distance between the patient and the breathing device. furthermore, mere one positioning rib 223 or positioning tab 231 is needed to allow a patient to adjust length of the breathing tube 92 while the breathing tube 92 is held.

Even though numerous characteristics and advantages of the present invention have been set forth in the foregoing description, together with details of the structure and function of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A tube-positioning device for a breathing mask comprising:
   a headgear buckle having
      two assembling holes defined through the headgear buckle; and
      a pivot bracket formed on the headgear buckle, located between the assembling holes and having
         a top;
         an outer surface;
         a pivot hole defined through the pivot bracket; and an annular groove defined radially in the outer surface; and
a tube retainer mounted rotatably and detachably on the headgear buckle and having
two resilient arms;
a pivot shaft formed on and protruding down from the resilient arms and mounted rotatably in the pivot hole of the pivot bracket,
wherein the resilient arms are curved and symmetrically extend outward from a top of the pivot shaft;
a clamping recess formed between the resilient arms; and
two hooking arms formed on and protruding respectively down from the resilient arms and each hooking arm having a hook formed on and protruding from the hooking arm and detachably engaging the annular groove of the pivot bracket of the headgear buckle;
wherein pressing the resilient arms toward each other disengages the hooks of the hooking arms from the annular groove of the pivot bracket.

2. The tube-positioning device as claimed in claim 1, wherein a height of the annular groove along an axis of the pivot bracket is larger than a height of the hook of each hooking arm to make the hook to hook in the annular groove.

3. The tube-positioning device as claimed in claim 1, wherein
the pivot bracket further has a recess being funnel-shaped, defined in the top, communicating with the pivot hole and having an annular inclined surface and multiple positioning slots defined in the annular inclined surface; and
the tube retainer further has at least one positioning stub formed respectively on the resilient arms and detachably engaging the positioning slots respectively.

4. The tube-positioning device as claimed in claim 1, wherein
each resilient arm has a top end; and
two resilient tabs are curved and formed respectively on the top ends of the resilient arm, each resilient tab is thinner than each resilient arm and has an inside convex surface and an outside concave surface; and
at least one positioning rib is formed on the inside at least one of the inside convex surfaces of the resilient tabs.

5. The tube-positioning device as claimed in claim 1, wherein the clamping recess further has a positioning tab formed on the top of the pivot shaft in the clamping recess.

6. The tube-positioning device as claimed in claim 1, wherein the headgear buckle further has
two opposite first sides;
two opposite second sides;
two crossbeams formed between the first sides and located respectively above the assembling holes; and
the pivot bracket is located between the crossbeams.

7. The tube-positioning device as claimed in claim 6, wherein a thickness of an intervening section between a central section of each first side and a jointing section at which one crossbeam is connected to the first side is smaller than thicknesses of the central section.

8. The tube-positioning device as claimed in claim 1, wherein each resilient arm further has an out side surface and a skidproof section formed on the outside surface.

9. The tube-positioning device as claimed in claim 6, wherein each second side of the headgear buckle has a bottom surface and a skidproof member formed on the bottom surface.

10. The tube-positioning device as claimed in claim 4, wherein the positioning ribs of the resilient arm are staggered along a front-rear direction.

* * * * *